United States Patent [19]

Sato et al.

[11] Patent Number: 5,322,842

[45] Date of Patent: Jun. 21, 1994

[54] TRICYCLIC BENZODIAZEPINE DERIVATES, THEIR PREPARATION, AND PHARMACEUTICAL COMPOSITIONS CONTAINING THEM

[75] Inventors: Yoshinari Sato, Takaishi; Teruaki Matuo, Ikeda; Takatomo Ogahara, Hiroshima, all of Japan

[73] Assignee: Fujisawa Pharmaceutical Co., Ltd., Osaka, Japan

[21] Appl. No.: 971,830

[22] PCT Filed: Aug. 22, 1991

[86] PCT No.: PCT/JP91/01112

§ 371 Date: Feb. 19, 1993

§ 102(e) Date: Feb. 19, 1993

[87] PCT Pub. No.: WO92/03438

PCT Pub. Date: Mar. 5, 1992

[30] Foreign Application Priority Data

Aug. 24, 1990 [GB] United Kingdom ............... 9018601

[51] Int. Cl.$^5$ ................... A61K 31/55; C07D 487/04
[52] U.S. Cl. .................................... 514/220; 540/497
[58] Field of Search ................... 540/497; 514/220

[56] References Cited

U.S. PATENT DOCUMENTS 4,929,614 5/1990 Calvet et al. ............... 540/497
4,981,847 1/1991 Sato et al. ............... 540/497
5,155,101 10/1992 Sato et al. ............... 540/497

FOREIGN PATENT DOCUMENTS 0340064 11/1989 European Pat. Off. ............ 540/497
0360079 3/1990 European Pat. Off. ............ 540/497

Primary Examiner—Robert T. Bond
Attorney, Agent, or Firm—Oblon, Spivak, McClelland, Maier & Neustadt

[57] ABSTRACT

Tricyclic compounds of the formula:

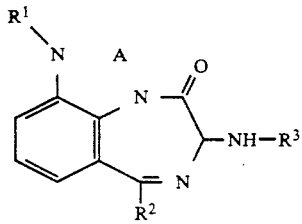

wherein
$R^1$ 1 is hydrogen or an organic group,
$R^2$ is aryl which may have suitable substituent(s),
$R^3$ is hydrogen or an acyl group and
A is lower alkylene, and pharmaceutically acceptable salts thereof which are useful as a medicament.

10 Claims, No Drawings

TRICYCLIC BENZODIAZEPINE DERIVATES, THEIR PREPARATION, AND PHARMACEUTICAL COMPOSITIONS CONTAINING THEM

TECHNICAL FIELD

This invention relates to new tricyclic compounds and pharmaceutically acceptable salts thereof which are useful as a medicament.

BACKGROUND ART

Some tricyclic compounds have been known as described, for example, in EP 0360079A1.

DISCLOSURE OF INVENTION

This invention relates to new tricyclic compounds and pharmaceutically acceptable salts thereof.

More particularly, it relates to new tricyclic compounds and pharmaceutically acceptable salts thereof which are cholecystokinin (CCK) antagonists and therefore useful as therapeutical and/or preventive agents for emesis, pancreatitis, disorders of appetite regulatory systems, pain, insulinoma, gastroparesis, carcinoma of pancreas, gallbladder disease (e.g. acute cholecystitis, calculus, etc.), disorders associated with intestinal smooth muscle hyperactivity (e.g. irritable bowel syndrome, sphincter spasm, etc.), hyperinsulinemia, dyspepsia, nausea, etc.

The tricyclic compounds of this invention can be represented by the following formula (I):

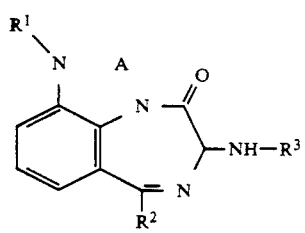

(I)

wherein
$R^1$ is hydrogen or an organic group,
$R^2$ is aryl which may have suitable substituent(s),
$R^3$ is hydrogen or an acyl group, and
A is lower alkylene.

According to the present invention, the new tricyclic compounds (I) can be prepared by the processes which are illustrated in the following scheme.

Process 1

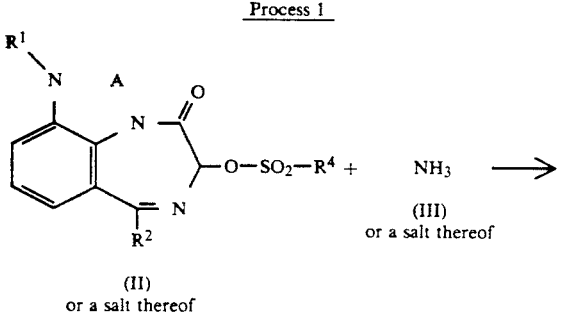

(II)
or a salt thereof

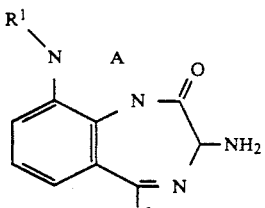

(Ia)
or a salt thereof

Process 2

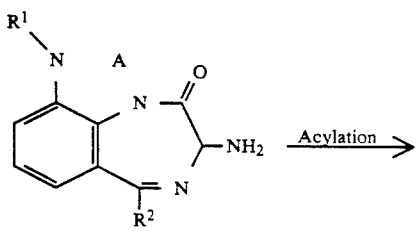

(Ia)
or its reactive derivative
at the amino group, or
a salt thereof

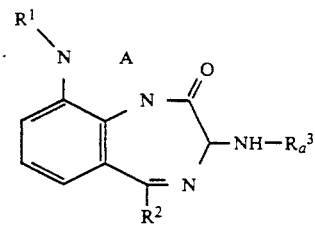

(Ib)
or a salt thereof

Process 3

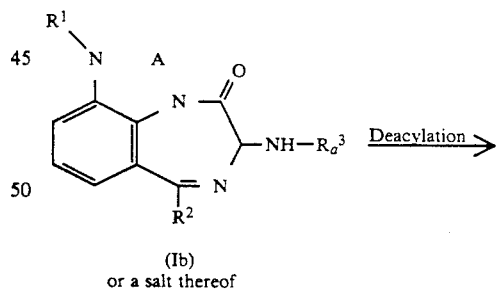

(Ib)
or a salt thereof

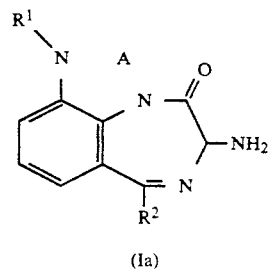

(Ia)
or a salt thereof

Process 4

-continued

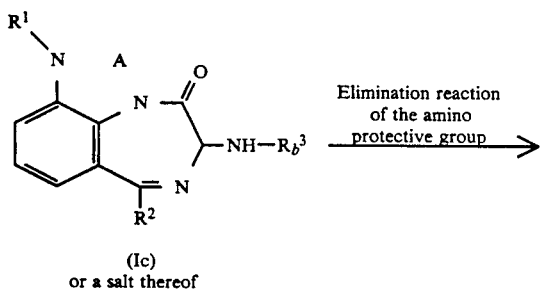

(Ic)
or a salt thereof

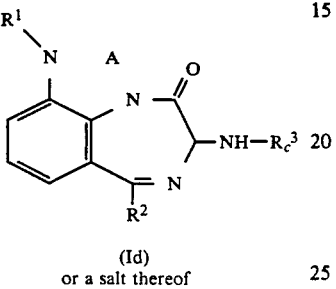

(Id)
or a salt thereof wherein
$R^1$, $R^2$ and A are each as defined above,
$R^4$ is an organic group,
$R_a^3$ is an acyl group,
$R_b^3$ is an acyl group having a protected amino group and
$R_c^3$ is an acyl group having an amino group.

The starting compound (II) is novel and can be prepared by the following processes.

Process A

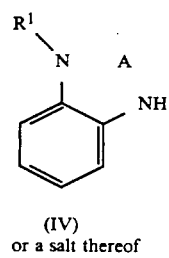

(IV)
or a salt thereof

① | $R^2$—CN
(V)
or a salt thereof

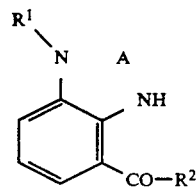

(VI)
or a salt thereof

② | $X^1$—CO—CH$_2$X$^2$
(VII)

-continued

Process A

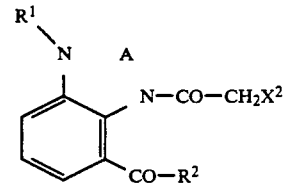

(VIII)
or a salt thereof

③ | H$_2$N—OH
(IX)
or a salt thereof

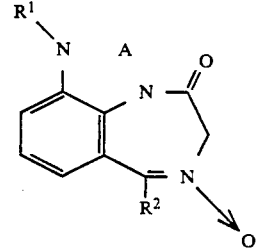

(X)
or a salt thereof

④ | (R$^5$—CO)$_2$O
(XI)

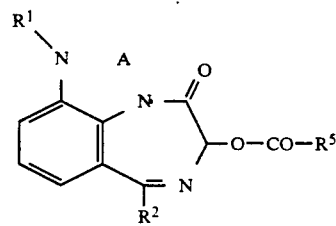

(XII)
or a salt thereof

⑤ | Hydrolysis

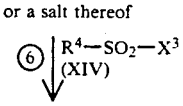

(XIII)
or a salt thereof

⑥ | R$^4$—SO$_2$—X$^3$
(XIV)

-continued
Process A

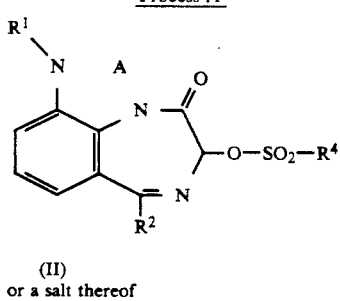

(II)
or a salt thereof wherein
$R^1$, $R^2$, $R^4$ and A are each as defined above,
$X^1$ is halogen,
$X^2$ is halogen,
$R^5$ is lower alkyl and
$X^3$ is halogen.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfoante, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated.

Suitable "organic group" may include lower alkyl (e.g., methyl, ethyl, propyl, isopropyl, butyl, isobutyl, tert-butyl, pentyl, neopentyl, tert-pentyl, hexyl, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), aryl (e.g., phenyl, naphthyl, etc.), ar(lower)alkyl such as phenyl(lower)alkyl (e.g., benzyl, phenethyl, phenylpropyl, etc.) and the like.

Suitable "aryl" may include phenyl, naphthyl and the like.

Suitable "substituent" in the term "aryl which may have suitable substituent(s)" may include halogen, amino, lower alkoxy, mono(or di or tri)halo(lower)alkyl and the like.

Suitable "halogen" and "halogen moiety" in the term "mono(or di or tri)halo(lower)alkyl" may include chlorine, bromine, fluorine and iodine.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "lower alkyl" and "lower alkyl moiety" in the term "mono(or di or tri)halo(lower)alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atoms(s).

Suitable "acyl" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows: Carbamoyl; Aliphatic acyl such as lower or higher alkanoyl (e.g. formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkoxycarbonyl (e.g. methoxycarbonyl, ethoxycarbonyl, t-butoxycarbonyl, t-pentyloxycarbonyl, heptyloxycarbonyl, etc.); lower or higher alkanesulfonyl (e.g. methanesulfonyl, ethanesulfonyl, etc.); lower or higher alkoxysulfonyl (e.g. methoxysulfonyl, ethoxysulfonyl, etc.); or the like;

Aromatic acyl such as
aroyl (e.g. benzoyl, toluoyl, naphthoyl, etc.);
ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g. naphthylacetyl, naphthylpropanoyl, naphthylbutanoyl, etc.), etc.];
ar(lower)alkenoyl [e.g. phenyl(lower)alkenoyl (e.g. phenylpropenoyl, phenylbutenoyl, phenylmethacryloyl, phenylpentenoyl, phenylhexenoyl, etc.), naphthyl(lower)alkenoyl (e.g. naphthylpropenoyl, naphthylbutenoyl, naphthylpentenoyl, etc.), etc.];
ar(lower)alkoxycarbonyl [e.g. phenyl(lower)alkoxycarbonyl (e.g. benzyloxycarbonyl, etc.), etc.]; aryloxycarbonyl (e.g. phenoxycarbonyl, naphthyloxycarbonyl, etc.); aryloxy(lower)alkanoyl (e.g., phenoxyacetyl, phenoxypropionyl, etc.); arylcarbamoyl (e.g. phenylcarbamoyl, naphthylcarbamoyl, etc.); arylthiocarbamoyl (e.g. phenylthiocarbamoyl, etc.); arylglyoxyloyl (e.g. phenylglyoxyloyl, naphthylglyoxyloyl, etc.); arenesulfonyl (e.g. benzenesulfonyl, p-toluenesulfonyl, etc.); or the like;

Heterocyclic acyl such as heterocycliccarbonyl; heterocyclic (lower)alkanoyl (e.g. thienylacetyl, thienylpropanoyl, thienylbutanoyl, thienylpentanoyl, thienylhexanoyl, thiazolylacetyl, thiadiazolylacetyl, tetrazolylacetyl, etc.); heterocyclic(lower)alkenoyl (e.g. heterocyclicpropenoyl, heterocyclicbutenoyl, heterocyclicpentenoyl, heterocyclichexenoyl, etc.); heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl", heterocyclic(lower)alkenoyl and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; saturated 3 to 8-membered (more preferably 5 or 6-membered)heteromonocyclic group containing 1 to 4 nitrogen atom(s), for example pyrrolidinyl, imidazolidinyl, piperidino, piperazinyl, etc.; unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, cinnolinyl, quinoxalinyl, etc.; unsaturated 3 to 8-membered (more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.; saturated 3 to 8-membered [more preferably 5 or 6-membered)heteromonocyclic group containing 1 to 2 oxygen atom(s) and 1 to 3 nitrogen atom(s), for example, morpholinyl, sydnonyl, etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (more preferable 5 or 6-membered)-heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.; saturated 3 to 8-membered (more preferably 5 or 6-membered) heteromonocyclic group containing 1 to 2 sulfur atom(s) and 1 to 3 nitrogen atom(s), for example, thiazolidinyl, etc.; unsaturated 3 to 8-membered (more preferably 5 or 6-membered) heteromonocyclic group containing 1 to 2 sulfur atom(s), for example, thienyl, dihydrodithiinyl, dihydrodithionyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 to 6-membered) heteromonocyclic group containing an oxygen atom, for example, furyl, etc.; unsaturated 3 to 8-membered (more preferably 5 or 6-membered)heteromonocyclic group containing an oxygen atom and 1 to 2 sulfur atom(s), for example, dihydrooxathiinyl, etc.; unsaturated condensed heterocyclic group containing 1 to 2 sulfur atom(s), for example, benzothienyl, benzodithiinyl, etc.; unsaturated condensed heterocyclic group containing an oxygen atom and 1 to 2 sulfur atom(s), for example, benzoxathiinyl, etc. and the like.

The acyl moiety as stated above may have one to ten, same or different, suitable substituent(s) such as halogen (e.g. fluorine, chlorine, bromine or iodine), hydroxy, nitro, lower alkyl (e.g. methyl, ethyl, propyl, isopropyl, butyl, isobutyl, t-butyl, pentyl, hexyl, etc.), amino, protected amino, lower alkoxy (e.g. methoxy, ethoxy, propoxy, butoxy, t-butoxy, pentyloxy, hexyloxy, etc.), carboxy, protected carboxy, N,N-di(lower)alkyl-amino(lower)alkyl (e.g. N,N-dimethylaminomethyl, N,N-diethylaminomethyl, N,N-dimethylaminoethyl, N,N-diethylaminoethyl, N,N-dipropylaminoethyl, N,N-dimethylaminopropyl, N,N-diethylaminopropyl, N,N-dipropylaminopropyl, N,N-dibutylaminomethyl, N,N-dipentylaminomethyl, N,N-dihexylaminomethyl, etc.), hydroxyimino(lower)alkyl (e.g. hydroxyiminomethyl, hydroxyiminoethyl, hydroxyiminopropyl, hydroxyiminobutyl, hydroxyiminopentyl, hydroxyiminohexyl, etc.), arylimino(lower)alkyl [e.g. phenylimino(lower)alkyl (e.g. phenyliminomethyl, phenyliminoethyl, phenyliminopropyl, phenyliminobutyl, phenyliminopentyl, phenyliminohexyl, etc.), etc.], acyl such as lower alkanoyl (e.g. formyl, acetyl, propanoyl, butanoyl, pentanoyl, hexanoyl, etc.), mono(or di or tri)halo(lower)alkyl, arylamino(e.g. phenylamino, etc.), or the like.

Suitable "protected amino" may include acylamino and the like.

Suitable "acyl moiety" in the term "acylamino" can be referred to the ones as mentioned above.

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl 2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono(or di or tri)-phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Suitable "lower alkylene" may include straight or branched one having 1 to 6 carbon atom(s), such as methylene, ethylene, trimethylene, tetramethylene, pentamethylene, hexamethylene or the like, preferably one having 1 to 4 carbon atoms(s).

Preferred embodiments of the object compound (I) are as follows:

$R^1$ is lower alkyl [more preferably ($C_1$–$C_4$)alkyl, most preferably methyl], $R^2$ is aryl (more preferably phenyl) which may have one to three suitable substituent(s) [more preferably phenyl which may have halogen, most preferably halophenyl], $R^3$ is hydrogen; or an organic carboxylic or an organic carbamic acyl, for example, heterocycliccarbonyl [more preferably unsaturated 5 or 6-membered heteromonocycliccarbonyl in which heteromonocyclic group contains 1 to 4 nitrogen atom(s) or unsaturated condensed heterocycliccarbonyl in which heterocyclic group contains 1 to 4 nitrogen atom(s), most preferably pyridylcarbonyl, indolylcarbonyl, quinolylcarbonyl, isoquinolylcarbonyl, cinnolinylcarbonyl or quinoxalinylcarbonyl], aroyl (more preferably benzoyl or naphthoyl) which may have one to three (more preferably one or two) suitable substituent(s) [more preferably benzoyl which may have one or two halogen, or naphthoyl; most preferably dihalobenzoyl or naphthoyl], arylcarbamoyl (more preferably phenylcarbamoyl) which may have one to three suitable substituent(s) [more preferably phenylcarbamoyl which may have lower alkyl, most preferably lower alkylphenylcarbamoyl], or ar(lower)alkanoyl (more preferably phenyl(lower)alkanoyl)- which may have one to three suitable substituent(s) [more preferably phenyl(lower)alkanoyl which may have amino or protected amino, most preferably phenyl(lower)alkanoyl having amino or acylamino], and A is lower alkylene [more preferably $(C_1-C_4)$alkylene, most preferably ethylene].

The processes for preparing the object compound (I) of the present invention are explained in detail in the following.

Process 1

The compound (Ia) or a salt thereof can be prepared by reacting the compound (II) or a salt thereof with the compound (III) or a salt thereof.

Suitable salts of the compounds (Ia) and (II) can be referred to the ones as exemplified for the compound (I).

Suitable salts of the compound (III) can be referred to the acid addition salts as exemplified for the compound (I).

This reaction is usually carried out in a solvent such as water alcohol (e.g., methanol, ethanol, etc.), benzene, N,N-dimethylformamide, tetrahydrofuran, methylene chloride, ethylene chloride, chloroform, diethyl ether, acetonitrile, or any other solvent which does not adversely affect the reaction.

The reaction temperature is not critical and the reaction is usually carried out under cooling to warming.

Process 2

The compound (Ib) or a salt thereof can be prepared by subjecting the compound (Ia) or its reactive derivative at the amino group or a salt thereof to acylation reaction.

Suitable acylating agent to be used in the present acylation reaction may include the compound of the formula:

$R_a^3$—OH     (XV)

(wherein $R_a^3$ is as defined above.) or its reactive derivative or a salt thereof.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as N,O-bis(trimethylsilyl)acetamide, N-trimethylsilylacetamide or the like; a derivative formed by the reaction of the compound (Ia) with phosphorus trichloride or phosgene, and the like.

Suitable salts of the compounds (Ia) and (XV) can be referred to the ones as exemplified for the compound (I).

Suitable reactive derivative of the compound (XV) may include an acid halide, an acid anhydride, an activated amide, an activated ester, isocyanate, and the like. The suitable example may be an acid chloride an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl $[(CH_3)_2N^+=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate; and the like. These reactive derivatives can optionally be selected from them according to the kind of the compound (XV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (XV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine, diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxasolium salt; 2-ethyl-5-(m-sulfophenyl)isoxazolium hydroxide intra-molecular salt; 1-(p-chlorobenzenesulfonyloxy)-6-chloro-1H-benzotirazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling to heating.

Process 3

The compound (Ia) or a salt thereof can be prepared by subjecting the compound (Ib) or a salt thereof to deacylation reaction. Suitable method of this reaction may include conventional one such as hydrolysis, reduction and the like.

(i) For Hydrolysis

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For reduction

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process ④

The compound (Id) or a salt thereof can be prepared by subjecting the compound (Ic) or a salt thereof to elimination reaction of the amino protective group. This reaction can be carried out in a similar manner to that of aforementioned Process 3.

The processes for preparing the starting compound (II) are explained in the following.

Process A - ①

The compound (VI) or a salt thereof can be prepared by reacting a compound (IV) or a salt thereof with a compound (V) or a salt thereof in accordance with the method disclosed in the Preparation 1 described later or a similar manner thereto.

Process A - ②

The compound (VIII) or a salt thereof can be prepared by reacting a compound (VI) or a salt thereof with a compound (VII).

This reaction can be carried out in accordance with the method disclosed in the Preparation 2 described later or a similar manner thereto.

Process A - ③

The compound (X) or a salt thereof can be prepared by reacting a compound (VIII) or a salt thereof with a compound (IX) or a salt thereof.

This reaction can be carried out in accordance with the method disclosed in the Preparation 3 described later or a similar manner thereto.

Process A - ④

The compound (XII) or a salt thereof can be prepared by reacting a compound (X) or a salt thereof with a compound (XI).

This reaction can be carried out in the presence or absence of a conventional solvent.

The reaction temperature is not critical and the reaction is usually carried out at ambient temperature, under warming or under heating.

Process A - ⑤

The compound (XIII) or a salt thereof can be prepared by subjecting a compound (XII) or a salt thereof to hydrolysis.

The hydrolysis can be carried out in the presence of a base, and suitable base may be the inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.) or the like.

This reaction is usually carried out in a solvent such as water, alcohol (e.g., methanol, ethanol, etc.), benzene, N,N-dimethylformamide, tetrahydrofuran, diethyl ether or any other solvent which does not adversely affect the reaction.

The reaction temperature is not critical and the reaction is usually carried out under cooling to warming.

Process A - ⑥

The compound (II) or a salt thereof can be prepared by reacting a compound (XIII) or a salt thereof with a compound (XIV).

This reaction is usually carried out in the presence of a base such as tri(lower)alkylamine (e.g., trimethylamine, triethylamine, diisopropylethylamine, etc.), di(lower)alkylaniline (e.g., dimethylaniline, etc.) or the like.

This reaction is usually carried out in a solvent such as benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to warming.

The object compound (I) and pharmaceutically acceptable salts thereof are CCK antagonists and therefore useful as therapeutical agents for emesis, pancreatitis, etc. Further, it is expected that the object compound (I) and pharmaceutically acceptable salts thereof have gastrin antagonism and are useful as therapeutical and/or preventive agents for ulcers, excess gastric secretion, zollinger-Ellison Syndrome, etc.

In order to show the utility of the object compound (I), pharmacological activity of the representative compound thereof is shown in the following.

[I] Test compound
(6RS)-1-Methyl-5-oxo-6-(2-indolylcarbonylamino)-8-(2-fluorophenyl)-2,3,5,6-tetrahydro-1H-[1,4]diazepino-[1,7,6-de]quinoxaline

[II] Test:
[$^{125}$I ] CCK-8 binding to rat pancreatic membranes

Test Method (i) Membrane preparation

Rats were killed by a blow on the head and bled to death. Whole pancreas (about 0.7 g) was removed, minced in a small quantity of 50 mM Tris-HCl buffer (pH 7.4), and homogenized in 30 vol: of the buffer by a polytron homogenizer. The homogenate was centrifuged at 30000×g (16000 rpm) for 10 min. The pellet was then resuspended in the same buffer by a glass-teflon homogenizer and recentrifuged at 30000×g for 10 min. This procedure (washings) was repeated twice more. The final pellet (membrane) was suspended in incubation medium (see below) so as to obtain a final protein concentration of 2 mg/ml. All manipulations were done at 0°–4° C.

(ii) Receptor binding assay

The composition of incubation medium was as follows: 50 mM Tris-HCl (pH 7.4), 5 mM $MgCl_2$, 5 mM dithiothreitol (DTT), 0.14 mg/ml bacitracin, and 0.2% bovine serum albumin (BSA). Freshly prepared membranes (200 µg protein) were incubated for 30 min under shaking at 37° C. in plastic tubes in 500 µl of incubation medium with 50 pM $^{125}$I-CCK-8 in the presence or absence of test compound ($1 \times 10^{-8}$M). To determine the non-specific binding, CCK-8 at 1 µM was added. Each assay was performed in duplicate. Reaction mixture was filtered through a Whatman GF/B glass filter to stop the reaction. After washing the filter with 50 mM Tris-HCl (pH 7.4) buffer containing 0.1% BSA, the radioactivity of the filter was counted. Non-specific binding was subtracted from total binding to yield specific binding. The effect of test compound was expressed as % inhibition of specific $^{125}$I-CCK-8 binding.

Test Result

Inhibition (%): 95.7

The object compound (I) or pharmaceutically acceptable salts thereof can usually be administered to mammals including human being in the form of a conventional pharmaceutical composition such as capsule, micro-capsule, tablet, granule, powder, troche, syrup, aerosol, inhalation, solution, injection, suspension, emulsion, suppository or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, organge powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of. 0.01 mg/kg to 50 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

To a solution of 2N-boron trichloride in benzene (82 ml) was dropwise added a solution of 1-methyl-1,2,3,4-tetrahydroquinoxaline (19.87 g) in toluene (40 ml) under stirring. To the resultant mixture was dropwise added a solution of 2-fluorobenzonitrile (19.50 g) in toluene (30 ml) at ambient temperature under stirring and the mixture was stirred for 1.5 hours under the same condition. To this mixture was added aluminum trichloride (19.65 g) and the mixture was refluxed for 16 hours. Water (30 ml) and 2N-hydrochloric acid (100 ml) were added to the reaction mixture under cooling in an ice-bath and the mixture was refluxed for 2.5 hours. After the mixture was allowed to stand at ambient temperature for several hours, ethyl acetate was added to the mixture. The organic layer was separated, washed with water twice, dried over magnesium sulfate and evaporated under reduced pressure. The residue was chromatographed on silica gel with an eluent of n-hexane. The fractions containing the desired product were combined and evaporated. The resultant red oil was crystallized with diisopropyl ether, collected by filtration and dried to give 1-methyl-5-(2-fluorobenzoyl)-1,2,3,4-tetrahydroquinoxaline (11.71 g).

mp: 90°-92° C.

IR (Nujol): 3275, 1608, 1520, 1480, 1458, 1442, 1380, 1305, 1275, 1240, 1203, 1127, 978, 755, 726 cm$^{-1}$ NMR (CDCl$_3$, δ): 2.89 (3H, s), 3.23 (2H, t, J=2.6 Hz), 3.71 (2H, m), 6.36-6.77 (3H, m), 7.1-7.4 (4H, m), 9.28 (1H, broad s)

Preparation 2

To a solution of 1-methyl-5-(2-fluorobenzoyl)-1,2,3,4-tetrahydroquinoxaline (11.99 g) and pyridine (4.04 g) in methylene chloride (200 ml) was dropwise added a solution of bromoacetyl bromide (5.09 ml) in methylene chloride (10 ml) under stirring at a temperature below 10° C. and the mixture was stirred for 3 hours at the same temperature. The reaction mixture was washed with water twice and dried. Removal of the solvent afforded viscous oil. The viscous oil was triturated with diisopropyl ether, collected by filtration, washed with diisopropyl ether and dried to give 1-methyl-4-bromoacetyl-5-(2-fluorobenzoyl)-1,2,3,4-tetrahydroquinoxaline (17.18 g).

IR (Nujol): 1675 (sh), 1662, 1607, 1586, 1500, 1460, 1402, 1335, 1295, 1212, 769, 751 cm$^{-1}$ NMR (CDCl$_3$, δ): 3.25 (3H, s), 3.73 (2H, s), 2.7-4.6 (4H, m), 6.6-7.8 (7H, m)

Preparation 3

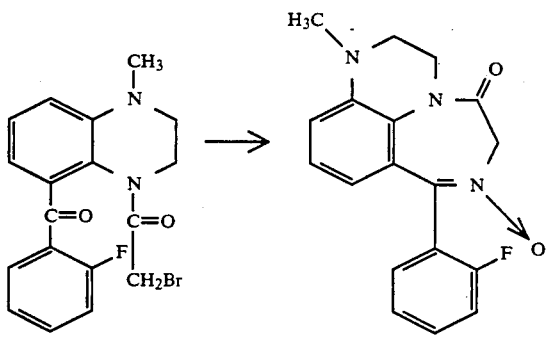

To a solution of sodium hydroxide (7.92 g) and hydroxylamine hydrochloride (15.75 g) in a mixture of water (80 ml) and ethanol (80 ml) was added a suspension of 1-methyl-4-bromoacetyl-5-(2-fluorobenzoyl)-1,2,3,4-tetrahydroquinoxaline (17.18 g) in ethanol (40 ml) portionwise under stirring at 50° C. The mixture was stirred for 2 hours at the same temperature and cooled in an ice-bath for 1 hour. The resultant precipitate was collected by filtration, washed with a small amount of cold ethanol and dried to give 1-methyl-5-oxo-8-(2-fluorophenyl)-2,3,5,6-tetrahydro-1H-[1,4]diazepino-[1,7,6-de]quinoxaline 7-oxide (7.47 g).

mp: 205°-206° C. (dec.)

IR (Nujol): 1662, 1609, 1583, 1532, 1493, 1451, 1403, 1335, 1197, 1062, 887, 788, 750 cm$^{-1}$ NMR (DMSO-d$_6$, δ): 3.01 (3H, s), 3.0-3.1 (1H, m), 3.4-3.5 (2H, m), 4.39 (1H, d, J=6.3 Hz), 4.75 (1H, dt, J=4.6 Hz, 13 Hz), 4.89 (1H, d, J=6.3 Hz), 6.16 (1H, d, J=3.3 Hz), 6.80 (1H, d, J=3.3 Hz), 7.04 (1H, t, J=4.0 Hz), 7.2-7.6 (4H, m)

MASS: m/e=325 (M+)

Preparation 4

A suspension of 1-methyl-5-oxo-8-(2-fluorophenyl)-2,3,5,6-tetrahydro-1H-[1,4]diazepino[1,7,6-de]quinoxaline 7-oxide (7.44 g) in acetic anhydride (50 ml) was stirred for 45 minutes at 95°-100° C. The mixture was cooled in an ice-bath and added diisopropyl ether (50 ml). The mixture was stirred under cooling in an ice-bath for 1 hour. The resultant precipitate was collected by filtration and washed with cold diisopropyl ether to afford (6RS)-1-methyl-5-oxo-6-acetoxy-8-(2-fluorophenyl)-2,3,5,6-tetrahydro-1H-[1,4]diazepino[1,7,6-de]-quinoxaline (7.58 g) as yellow crystalline powder.

mp: 201°-202° C.

IR (Nujol): 1741, 1690, 1600, 1584, 1455, 1400, 1373, 1229, 1114, 1060, 765, 748 cm$^{-1}$ NMR (DMSO-d$_6$, δ): 2.20 (3H, s), 3.02 (3H, s), 2.9-3.1 (1H, m), 3.3-3.5 (2H, m), 4.69 (1H, d, J=6.3 Hz), 5.83 (1H, s), 6.39 (1H, d, J=3.5 Hz), 6.92 (1H, d, J=3.5 Hz), 7.0-7.6 (5H, m)

MASS: m/e=367 (M+)

Preparation 5

To a suspension of (6RS)-1-methyl-5-oxo-6-acetoxy-8-(2-fluorophenyl)-2,3,5,6-tetrahydro-1H-[1,4]diazepino-[1,7,6-de]quinoxaline (7.55 g) in ethanol (190 ml) was added 1N-sodium hydroxide (20.6 ml) under stirring at ambient temperature. The clear solution was stirred for 10 minutes. The mixture was adjusted to pH 6 with 6N-hydrochloric acid and ethanol was removed under reduced pressure. To the resultant mixture was added water (100 ml) and the mixture was adjusted to pH 7.0 with a saturated aqueous solution of sodium bicarbonate. The resultant yellow precipitate was collected by filtration, washed with water and dried over phosphorous pentoxide in desiccator under reduced pressure to give (6RS)-1-methyl-5-oxo-6-hydroxy-8-(2-fluorophenyl)-2,3,5,6-tetrahydro-1H-[1,4]diazepino[1,7,6-de]quinoxaline (6.54 g).

mp: 225°-227° C. (dec.)

IR (Nujol): 3375, 1664, 1610, 1578, 1491, 1551, 1428, 1388, 1373, 1332, 1152, 1027, 880, 778, 742 cm$^{-1}$ NMR (DMSO-d$_6$, δ): 2.99 (3H, s), 2.9-3.1 (1H, m), 3.4-3.5 (2H, m), 4.73 (1H, dt, J=5.0 Hz, 1.4 Hz), 4.84 (1H, s), 6.3-7.6 (8H, m)

MASS: m/e=325 (M+)

EXAMPLE 1

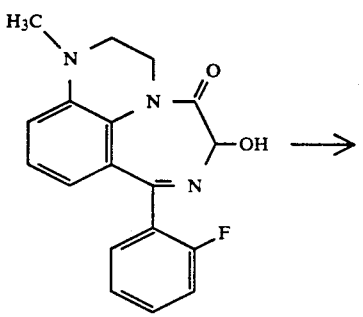

-continued

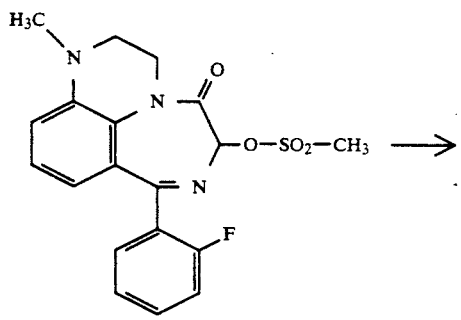

EXAMPLE 2

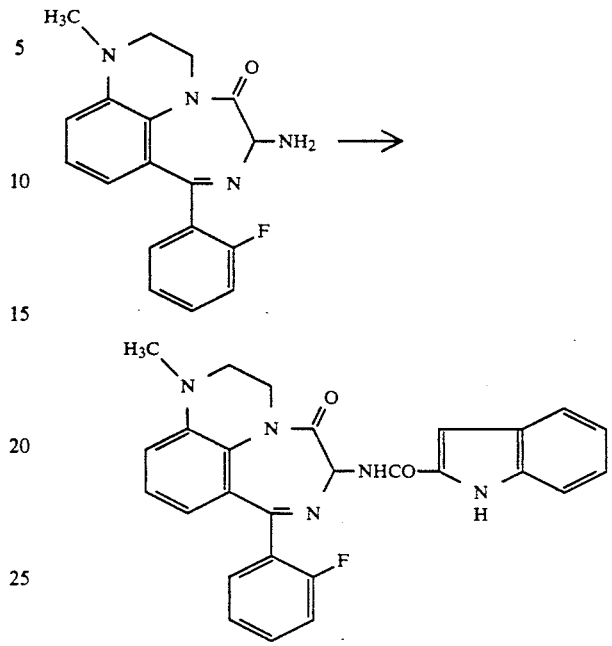

To a suspension of (6RS)-1-methyl-5-oxo-6-hydroxy-8-(2-fluorophenyl)-2,3,5,6-tetrahydro-1H-[1,4]diazepino-[1,7,6-de]quinoxaline (1.63 g) and diisopropylethylamine (0.97 g) in methylene chloride (15 ml) was added dropwise a solution of mesyl chloride (0.86 g) in methylene chloride (1 ml) under stirring and cooling in an ice-bath. The mixture was stirred for 15 minutes under the same conditions and for 30 minutes at ambient temperature. The reaction mixture containing (6RS)-1-methyl-5-oxo-6-mesyloxy- 8-(2-fluorophenyl)-2,3,5,6-tetrahydro-1H-[1,4]-diazepino[1,7,6-de]quinoxaline was poured into a mixture of 28% aqueous ammonia (8.2 ml) and acetonitrile (16.5 ml) at ambient temperature with a vigorous stirring and the mixture was stirred for 1 hour. From the reaction mixture, methylene chloride and acetonitrile were removed under reduced pressure. Water was added to the residual aqueous mixture. The mixture was extracted with chloroform twice. The chloroform layer was combined washed with water twice and dried over magnesium sulfate. Removal of the solvent afforded viscous brown oil, which was chromatographed on silica gel with an eluent of a mixture of chloroform and methanol (100:1). The fractions containing the desired product were combined and evaporated to give (6RS)-1-methyl-5-oxo-6-amino-8-(2-fluorophenyl)-2,3,5,6-tetrahydro-1H-[1,4]diazepino-[1,7,6-de]quinoxaline (0.88 g) as orange oil.

NMR (CDCl$_3$, δ): 2.41 (2H, broad s), 3.01 (3H, s), 2.6–3.2 (1H, m), 3.3–3.7 (2H, m), 4.58 (1H, s), 3.9–5.0 (1H, m), 6.4–7.7 (7H, m)

MASS: m/e=324 (M$^+$)

To a mixture of (6RS)-1-methyl-5-oxo-6-amino-8-(2-fluorophenyl)-2,3,5,6-tetrahydro-1H-[1,4]diazepino-[1,7,6-de]quinoxaline (0.73 g), indole-2-carboxylic acid (0.36 g) and 1-hydroxybenzotriazole (0.30 g) in N,N-dimethylformamide (10 ml) were added N-ethyl-N'-(3-dimethylaminopropyl)carbodiimide hydrochloride (0.43 g) and triethylamine (0.23 g) under stirring and cooling in an ice-bath. The mixture was stirred at ambient temperature for 2.0 hours. The reaction mixture was poured into a mixture of ice-water (100 ml) and ethyl acetate (30 ml) under vigorous stirring. The resultant precipitate was collected by filtration and washed with a small amount of cold ethanol and ethyl acetate to give yellow crystalline powder (0.58 g). This powder was vigorously stirred in water to remove crystalline solvent for 5 days, collected by filtration and dried over phosphorus pentoxide under reduced pressure to give (6RS)-1-methyl-5-oxo-6-(2-indolylcarbonylamino)-8-(2-fluorophenyl)-2,3,5,6-tetrahydro-1H-[1,4]diazepino-[1,7,6-de]quinoxaline (0.52 g).

mp: 275°–280° C. (dec.)

NMR (CDCl$_3$, δ): 3.05 (3H, s), 3.0–3.2 (1H, m), 3.4–3.6 (2H, m), 4.96 (1H, broad d, J=6.4 Hz), 5.92 (1H, d, J=4 Hz), 6.5–8.1 (13H, m), 9.78 (1H, s)

MASS: m/e=467 (M$^+$)

EXAMPLE 3

The following compounds were obtained according to a similar manner to that of Example 2.

(1) (6RS)-1-Methyl-5-oxo-6-(3-quinolylcarbonylamino)-8-(2-fluorophenyl)-2,3,5,6-tetrahydro-1H-[1,4]-diazepino[1,7,6-de]quinoxaline mp: 246°–251° C. (dec.)

IR (Nujol): 3390, 1675, 1660, 1610, 1500, 1375, 1340, 1228, 1020, 884, 774, 775, 720 cm$^{-1}$ NMR (DMSO-d$_6$, δ): 3.05 (3H, s), 3.0–3.2 (1H, m), 3.4–3.6 (2H, m), 4.77 (1H, broad d, J=6.2 Hz), 5.71 (1H, d, J=4.0 Hz), 6.44 (1H, d, J=3.4 Hz), 6.96 (1H, d, J=3.4 Hz), 7.0–8.2 (9H, m), 9.06 (1H, d, J=1.0 Hz), 9.37 (1H, d, J=1.0 Hz), 10.08 (1H, d, J=4.0 Hz)

MASS: m/e=479 (M+)

(2) (6RS)-1-Methyl-5-oxo-6-(2-naphthylcarbonylamino)-8-(2-fluorophenyl)-2,3,5,6-tetrahydro-1H-[1,4]-diazepino[1,7,6-de]quinoxaline mp: 142°–145° C. (dec.)

IR (Nujol): 3200, 1660 (sh), 1656, 1625, 1600, 1495, 1400, 1375, 1337, 1286, 871, 780, 763, 745 cm$^{-1}$ NMR (DMSO-d$_6$, δ): 3.05 (3H, s), 3.0–3.2 (1H, m), 3.4–3.6 (2H, m), 4.77 (1H, broad d, J=6.2 Hz), 5.72 (1H, d, J=6.0 Hz), 6.44 (1H, d, J=3.5 Hz), 6.95 (1H, d, J=3.5 Hz), 7.0–8.1 (11H, m), 8.71 (1H, s), 9.76 (1H, d, J=4.0 Hz)

MASS: m/e=478 (M+)

(3) (6RS)-1-Methyl-5-oxo-6-(3,4-dichlorobenzoylamino)-8-(2-fluorophenyl)-2,3,5,6-tetrahydro-1H-[1,4]-diazepino[1,7,6-de]quinoxaline mp: 215°–218° C.

IR (Nujol): 3200, 1691, 1647, 1610, 1595, 1530, 1375, 1345, 1280, 1183, 876, 781, 749 cm$^{-1}$ NMR (DMSO-d$_6$, δ): 3.04 (3H, s), 3.0–3.1 (1H, m), 3.4–3.6 (2H, m), 4.74 (1H, broad d, J=6.1 Hz), 5.62 (1H, d, J=4.0 Hz), 6.42 (1H, d, J=3.5 Hz), 6.94 (1H, d, J=3.5 Hz), 7.0–8.3 (9H, m), 9.96 (1H, d, J=4.0 Hz)

MASS: m/e=497 (M+)

(4) (6RS)-1-Methyl-5-oxo-6-nicotinoylamino-8-(2-fluorophenyl)-2,3,5,6-tetrahydro-1H-[1,4]diazepino-[1,7,6-de]quinoxaline dihydrochloride mp: 185°–190° C. (dec.)

IR (Nujol): 3600–3100, 2700–1900, 1670, 1630, 1610. 1580 cm$^{-1}$

NMR (DMSO-d$_6$, δ): 3.04–3.50 (6H, m), 4.75 (1H, d, J=12.3 Hz), 5.65 (1H, d, J=7.6 Hz), 6.48 (1H, d, J=7.3 Hz), 6.94–8.09 (7H, m), 8.89 (1H, d, J=8.1 Hz), 9.03 (1H, d, J=5.3 Hz), 9.36 (1H, s), 10.35 (1H, d, J=7.6 Hz)

MASS: m/e=429 (M+ −73)

(5) (6RS)-1-Methyl-5-oxo-6-(1-isoquinolylcarbonylamino)-8-(2-fluorophenyl)-2,3,5,6-tetrahydro-1H-[1,4]-diazepino[1,7,6-de]quinoxaline hydrochloride mp: 160°–170° C. (dec.)

IR (Nujol): 3550–3100, 2700–2000, 1660, 1605, 1580 cm$^{-1}$

NMR (DMSO-d$_6$, δ): 2.95–3.16 (1H, m), 3.05 (3H, s), 3.39–3.51 (2H, m), 4.80 (1H, d, J=12.4 Hz), 5.65 (1H, d, J=7.9 Hz), 6.48 (1H, d, J=6.9 Hz), 6.95–8.18 (10H, m), 8.67 (1H, d, J=5.6 Hz), 9.19 (1H, d, J=8.5 Hz), 9.86 (1H, d, J=7.9 Hz)

MASS: m/e=479 (M+ −37), 462

(6) (6RS)-1-Methyl-5-oxo-6-(4-cinnolinylcarbonylamino)-8-(2-fluorophenyl)-2,3,5,6-tetrahydro-1H-[1,4]-diazepino[1,7,6-de]quinoxaline mp: 228°–230° C.

IR (Nujol): 3200, 1690, 1660, 1610, 1595, 1535 cm$^{-1}$

NMR (DMSO-d$_6$, δ): 2.95–3.63 (6H, m), 4.82 (1H, d, J=12.4 Hz), 5.72 (1H, d, J=7.6 Hz), 6.47 (1H, d, J=7.0 Hz), 6.99–8.60 (10H, m), 9.48 (1H, s), 10.41 (1H, d, J=7.6 Hz)

MASS: m/e=480 (M+)

(7) (6RS)-1-Methyl-5-oxo-6-(2-quinoxalinyl)-8-(2-fluorophenyl)-2,3,5,6-tetrahydro-1H-[1,4]diazepino-[1,7,6-de]quinoxaline mp: 278°–280° C.

IR (Nujol): 3350, 1670, 1610, 1575, 1515 cm$^{-1}$

NMR (DMSO-d$_6$, δ): 3.04–3.50 (6H, m), 4.79 (1H, d, J=12.4 Hz), 5.64 (1H, d, J=7.9 Hz), 6.47 (1H, d, J=7.2 Hz), 6.95–8.36 (10H, m), 9.53–9.60 (2H, m)

MASS m/e=480 (M+)

(8) (6S)-1-Methyl-5-oxo-6-(2-indolylcarbonylamino)-8-(2-fluorophenyl)-2,3,5,6-tetrahydro-1H-[1,4]-diazepino[1,7,6-de]quinoxaline mp: 187°–194° C. (dec.)

[α]$_D^{30}$=79.33° (C=0.808, CHCl$_3$)

IR (Nujol): 3370, 3205, 1678, 1640, 1532, 1490, 1458, 1338, 1216, 1190, 1120, 810, 745 cm$^{-1}$ NMR (DMSO-d$_6$, δ): 3.04 (3H, s), 3.0–3.1 (1H, m), 3.3–3.5 (2H, m), 4.76 (1H, broad d, J=6.2 Hz), 5 68 (1H, d, J=4.1 Hz), 6.4–7.7 (12H, m), 9.57 (1H, d, J=4.1 Hz), 11.64 (1H, s)

MASS: m/e=467 (M+)

(9) (6R)-1-Methyl-5-oxo-6-(2-indolylcarbonylamino)-8-(2-fluorophenyl)-2,3,5,6-tetrahydro-1H-[1,4]-diazepino[1,7,6-de]quinoxaline mp: 187°–210° C. (dec.)

[α]$_D^{30}$=−72.77° (C=0.808, CHCl$_3$)

IR (Nujol): 3370, 3200, 1676, 1638, 1531, 1489, 1456, 1336, 1220, 1189, 1118, 808, 745 cm$^{-1}$ NMR (DMSO-d$_6$, δ): 304 (3H, s), 3.0–3.1 (1H, m), 3.3–3.5 (2H, m), 4.76 (1H, broad d, J=6.2 Hz), 5.68 (1H, d, J=4.1 Hz), 6.4–7.7 (12H, m), 9.57 (1H, d, J=4.1 Hz), 11.64 (1H, s)

MASS: m/e=467 (M+)

EXAMPLE 4

To a solution of (6RS)-1-methyl-5-oxo-6-amino-8-(2-fluorophenyl)-2,3,5,6-tetrahydro-1H-[1,4]diazepino-[1,7,6-de]quinoxaline (0.7 g) in tetrahydrofuran (11 ml) was added m-tolyl isocyanate (0.32 g) under stirring at ambient temperature. The mixture was stirred for 1.5 hours under the same conditions. The solvent was removed under reduced pressure to give powder, which was purified by column chromatography on silica gel with an eluent of chloroform. The fractions containing the desired product were combined and evaporated. The residue was pulverized with diisopropyl ether, collected by filtration, washed with diisopropyl ether and dried under reduced pressure to give (6RS)-1-methyl-5-oxo-6-[N′-(m-tolyl)ureido]-8-(2-fluorophenyl)-2,3,5,6-tetrahydro-1H-[1,4]diazepino-[1,7,6-de]quinoxaline (0.8 g).

mp: 242°–245° C.

IR (Nujol): 3300, 1675, 1640, 1610, 1555 cm$^{-1}$

NMR (DMSO-d$_6$ δ): 2.24 (3H, s), 2.27 (1H, s), 2.91–3.60 (6H, m), 4.75 (1H, d, J=12.4 Hz), 5.33 (1H, d, J=7.2 Hz), 6.41 (1H, d, J=7.6 Hz), 6.73–7.56 (10H, m), 8.96 (1H, s)

EXAMPLE 5

A mixture of (6RS)-1-methyl-5-oxo-6-amino-8-(2-fluorophenyl)-2,3,5,6-tetrahydro-1H-[1,4]diazepino-[1,7,6-de]quinoxaline (9.27 g), N-t-butoxycarbonyl-L-phenylalanine (7.96 g), 1-hydroxybenzotriazole (3.97 g), N-ethyl-N′-(3-dimethylaminopropyl)carbodiimide hydrochloride (5.64 g) and triethylamine (2.97 g) in N,N-dimethylformamide (95 ml) was stirred for 2 hours at ambient temperature. To the reaction mixture were added ethyl acetate (200 ml) and water (150 ml) under vigorous stirring. The mixture was adjusted to pH 8. with a saturated aqueous solution of sodium bicarbonate. The separated organic layer and the extract from the aqueous layer with ethyl acetate (200 ml) were combined and washed with water twice. The dried extract was evaporated under reduced pressure to give crude organge oil (17.58 g) of a mixture of (6R)-1-methyl-5-oxo-6-[((2S)-2-tertbutoxycarbonylamino-3-phenylpropanoyl)amino]-8-(2-fluorophenyl)-2,3,5,6-tetrahydro-1H-[1,4]diazepino-[1,7,6-de]quinoxaline and (6S)-1-methyl-5-oxo-6-[((2S)-2-tert-butoxycarbonylamino-3- phenylpropanoyl)amino]-8-(2-fluorophenyl)-2,3,5,6-tetrahydro-1H-[1,4]diazepino-[1,7,6-de]quinoxaline.

NMR (CDCl₃, δ): 1.39, 1.40 (9H, s & s), 3.04, 3.05 (3H, s & s), 3.0–3.7 (6H, m), 4.57 (1H, broad s), 4.86, 4.93 (1H, broad q & broad q), 5.01 (1H, broad s), 5.58, 5.59 (1H, d & d, J=4 Hz), 6.5–7.7 (12H, m)

MASS: m/e=571 (M+)

EXAMPLE 6

A solution of a mixture (17.2 g) of (6R)-1-methyl-5-oxo-6-[((2S)-2-tert-butoxycarbonylamino-3-phenyl-propanoyl)amino]-8-(2-fluorophenyl)-2,3,5,6-tetrahydro-1H-[1,4]diazepino[1,7,6-de]quinoxaline and (6S)-1-methyl-5-oxo-6-[((2S)-2-tert-butoxycarbonylamino-3-phenylpropanoyl)amino]-8-(2-fluorophenyl)-2,3,5,6-tetrahydro-1H-[1,4]diazepino[1,7,6-de]quinoxaline in ethyl acetate (350 ml) was saturated with dried hydrogen chloride. The mixture was stirred for 3 hours at ambient temperature. Excess hydrogen chloride was removed as much as possible by bubbling with a stream of nitrogen. The resultant solution was extracted with water and with diluted hydrochloric acid. The combined aqueous extract was neutralized with a aqueous solution of sodium bicarbonate. An oily product was extracted with ethyl acetate twice and washed with water. After the extract was dried over magnesium sulfate, the solvent was removed under reduced pressure to give yellow oil (11.98 g) of a mixture of (6R)-1-methyl-5-oxo-6-[((2S)-2-amino-3-phenylpropanoyl)amino]-8-(2-fluorophenyl)-2,3,5,6-tetrahydro-1H-[1,4]diazepino[1,7,6-de]quinoxaline and (6S)-1-methyl-5-oxo-6-[((2S)-2-amino-3-phenylpropanoyl)-amino]-8-(2-fluorophenyl)-2,3,5,6-tetrahydro-1H-[1,4]-diazepino[1,7,6-de]quinoxaline.

EXAMPLE 7

A mixture (11.98 g) of (6R)-1-methyl-5-oxo-6-[((2S)-2-amino-3-phenylpropanoyl)amino]-8-(2-fluorophenyl)-2,3,5,6-tetrahydro-1H-[1,4]diazepino-[1,7,6-de]quinoxaline and (6S)-1-methyl-5-oxo-6-[((2S)-2-amino-3-phenylpropanoyl)amino]-8-(2-fluorophenyl)-2,3,5,6-tetrahydro-1H-[1,4]diazepino[1,7,6-de]quinoxaline was subjected to column chromatography on silica gel with an eluent of chloroform. The fractions containing the one isomer were combined and evaporated to give an yellow crystal of (6S)-1-methyl-5-oxo-6-[(2S)-2-amino-3-phenylpropanoyl)amino]-8-(2-fluorophenyl)-2,3,5,6-tetrahydro-1H-[1,4]diazepino[1,7,6-de]quinoxaline (4.12 g).

mp: 195°–198° C.

NMR (CDCl₃, δ): 1.55 (2H, s), 2.80 (1H, dd, J=5 Hz, 6.8 Hz), 3.05 (3H, s), 3.13 (1H, dd, J=1.7 Hz, 5 Hz), 3.3–3.8 (4H, m), 4.92 (1H, dq, J=6.3 Hz, 1 Hz), 5.66 (1H, d, J=4.3 Hz), 6.5–7.7 (12H, m), 8.98 (1H, d, J=4.3 Hz)

The fractions containing the other isomer were combined and evaporated to give orange oil of (6R)-1-methyl-5-oxo-6-[((2S)-2-amino-3-phenylpropanoyl)-amino]-8-(2-fluorophenyl)-2,3,5,6-tetrahydro-1H-[1,4]-diazepino[1,7,6-de]quinoxaline (4.89 g).

NMR (CDCl₃, δ): 1.56 (2H, s), 2.67 (1H, dd, J=5 Hz, 6.8 Hz), 3.05 (3H, s), 3.13 (1H, dd, J=1.8 Hz, 6.2 Hz), 3.3–3.8 (4H, m), 4.94 (1H, dq, J=5.3 Hz, 1 Hz), 5.64 (1H, d, J=4.3 Hz), 6.5–7.7 (12H, m), 9.0 (1H, d, J=4.2 Hz)

EXAMPLE 8

To a solution of (6S)-1-methyl-5-oxo-6-[((2S)-2-amino-3-phenylpropanoyl)amino]-8-(2-fluorophenyl)-2,3,5,6-tetrahydro-1H-[1,4]diazepino[1,7,6-de]quinoxaline (3.85 g) in methylene chloride (70 ml) was added phenyl isothiocyanate (1.32 g) under stirring at ambient temperature. The methylene chloride was distilled under stirring at 80° C. To the residue was added methylene chloride (70 ml). This procedure was repeated four times. From the reaction mixture, methylene chloride was removed completely under reduced pressure. To the residue was added trifluoroacetic acid (50 ml) and the mixture was warmed under stirring at 50° C. for 20 minutes. After removal of the solvent in vacuo, the residue was subjected to column chromatography on silica gel with an eluent of a mixture of chloroform and methanol (40:1→20:1). The fractions containing the desired product were combined and washed with an aqueous solution of sodium bicarbonate. After drying, solvent was removed in vacuo to give (6S)-1-methyl-5-oxo-6-amino-8-(2-fluorophenyl)-2,3,5,6-tetrahydro-1H-[1,4]diazepino[1,7,6-de]quinoxaline (2.99 g).

$[\alpha]_D^{29}=97.94°$ (C=0.54, MeOH)

NMR (CDCl₃, δ): 2.40 (2H, broad s), 3.04 (3H, s), 3.01–3.2 (1H, m), 3.3–3.65 (2H, m), 4.58 (1H, s), 4.9–5.0 (1H, m), 6.45–7.7 (7H, m)

EXAMPLE 9

The following compound was obtained according to a similar manner to that of Example 8.

(6R)-1-Methyl-5-oxo-6-amino-8-(2-fluorophenyl)-2,3,5,6-tetrahydro-1H-[1,4]diazepino[1,7,6-de]quinoxaline $[\alpha]_D^{29}=-89.77°$ (C=0.54, CH₃OH)

NMR (CDCl₃, δ): 2.46 (2H, broad s), 3.04 (3H, s), 3.01–3.2 (1H, m), 4.59 (1H, s), 4.9–5.0 (1H, m), 6.45–7.7 (7H, m)

We claim:

1. A compound of the formula:

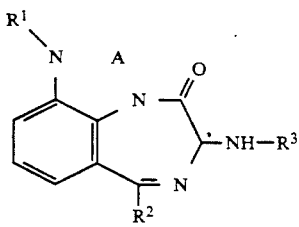

wherein

R¹ is hydrogen, or an organic group selected from the group consisting of lower alkyl, lower alkenyl, lower alkynyl, phenyl, naphthyl and phenyl(lower-)alkyl, R² phenyl or naphthyl, each of which may have from 1 to 3 substituents selected form the group consisting of halogen, amino, lower alkoxy and mon, di or tri halo(lower)alkyl, R³ is hydrogen, or an acyl group selected from the group consisting of carbamoyl, C1 to C20 alkanoyl, C2 to C20 alkoxycarbonyl, C1 to C20 alkanesulfonyl, C1 to C20 alkoxysulfonyl, benzoyl, naphthoyl, phenyl(lower)alkanoyl, naphthyl(lower)alkanoyl, phenyl(lower)alkenoyl, naphthyl(lower)alkenoyl, phenyl(lower)alkoxycarbonyl, phenoxycarbonyl, naphthyloxycarbonyl, phenylcarbamoyl, naphthylcarbamoyl, phenylthiocarbamoyl, phenylglyoxyloyl, naphthylglyoxyloyl, benzenesulfonyl, heterocyclicglyoxyloyl, heterocyclic(lower)alkanoyl, heterocyclic(lower)alkenoyl, and heterocycliccarbonyl wherein said heterocyclic moiety is selected form the group consisting of pyrrolyl, pyrrolinyl, imidazolyl, pyrazolyl, pyridyl, dihydropyridyl, pyrimidyl, pyrazinyl, pyridazinyl, triazolyl, tetrazolyl, pyrrolidinyl, imidazolidinyl, piperidino, piperazinyl, indolyl, isoindolyl, indolinyl, indolizinyl, benzimidazolyl, quinolyl, isoquinolyl, indazolyl, benzotriazolyl, cinnolinyl, quinoxalinyl, oxazolyl, isoxazolyl, oxadiazolyl, morpholinyl, sydnonyl, benzoxazolyl, benzoxadiazolyl, thiazolyl, isothiazolyl, thiadiazolyl, dihydrothiazinyl, thiazolidinyl, thienyl, dihydrodithiinyl, dihydrodithionyl, benzothiazolyl, benzothiadiazolyl, furyl, dihydrooxathiinyl, benzothienyl, benzodithiinyl and benzoxathiinyl, and said acyl group may have from 1 to 10 substituents selected from the group consisting of halogen, hydroxy, nitro, lower alkyl, amino, lower alkoxycarbonylamino, lower alkoxy, carboxy, N,N-di(lower)alkylamino(lower)alkyl, hydroxyimino(lower)alkyl, phenylimino(lower)alkyl, lower alkanoyl, mono, di or tri halo(lower)alkyl and phenylamino, and A is ethylene, and a pharmaceutically acceptable salt thereof.

2. A compound of claim 1, wherein
R$^1$ is hydrogen or lower alkyl, and
R$^3$ is hydrogen, heterocycliccarbonyl wherein said heterocyclic moiety is selected from the group consisting of pyrrolyl, pyrrolinyl, imidazolyl, pyrazolyl, pyridyl, dihydropyridyl, pyrimidyl, pyrazinyl, pyridazinyl, triazolyl, tetrazolyl, pyrrolidinyl, imidazolidinyl, piperidino, piperazinyl, indolyl, isoindolyl, indolinyl, indolizinyl, benzimidazolyl, quinolyl, isoquinolyl, indazolyl, benzotriazolyl, cinnolinyl, quinoxalinyl, oxazolyl, isoxazolyl, oxadiazolyl, morpholinyl, sydnonyl, benzoxazolyl, benzoxadiazolyl, thiazolyl, isothiazolyl, thiadiazolyl, dihydrothiazinyl, thiazolidinyl, thienyl, dihydrodithiinyl, dihydrodithionyl, benzothiazolyl, benzothiadiazolyl, furyl, dihydrooxathiinyl, benzothienyl, benzodithiinyl and benzoxathiinyl, benzoyl which may have from 1 to 3 substituents selected from the group consisting of halogen, hydroxy, nitro, lower alkyl, amino, lower alkoxycarbonylamino, lower alkoxy, carboxy, N,N-di(lower)alkylamino(lower)alkyl, hydroxyimino(lower)alkyl, phenylimino(lower)alkyl, lower alkanoyl, mono, di or tri halo(lower)alkyl and phenylamino, phenylcarbamoyl which may have from 1 to 3 substituents selected from the group consisting of halogen, hydroxy, nitro, lower alkyl, amino, lower alkoxycarbonylamino, lower alkoxy, carboxy, N,N-di(lower)alkylamino(lower)alkyl, hydroxyimino(lower)alkyl, phenylimino(lower)alkyl, lower alkanoyl, mono, di or tri halo(lower)alkyl and phenylamino, or phenyl(lower)alkanoyl which may have from 1 to 3 substituents selected from the group consisting of halogen, hydroxy, nitro, lower alkyl, amino, lower alkoxycarbonylamino, lower alkoxy, carboxy, N,N-di(lower)alkylamino(lower)alkyl, hydroxyimino(lower)alkyl, phenylimino(lower)alkyl, lower alkanoyl, mono di or tri halo(lower)alkyl and phenylamino.

3. A compound of claim 2, wherein
R$^2$ is phenyl which may have halogen and
R$^3$ is hydrogen, pyridylcarbonyl, indolylcarbonyl, quinolylcarbonyl, isoquinolylcarbonyl, cinnolinylcarbonyl, quinoxalinylcarbonyl, benzoyl which may have one or two halogen, naphthoyl, phenylcarbamoyl which may have lower alkyl, or phenyl(lower)alkanoyl which may have amino or lower alkoxy carbonylamino.

4. A compound of claim 3, wherein
R$^3$ is hydrogen, pyridylcarbonyl, indolylcarbonyl, quinolylcarbonyl, isoquinolylcarbonyl, cinnolinylcarbonyl, quinoxalinylcarbonyl, dihalobenzoyl, naphthoyl, lower alkylphenylcarbamoyl, or phenyl(lower)alkanoyl having amino or lower alkoxycarbonylamino.

5. A compound of claim 4, wherein
R$^1$ is lower alkyl,
R$^2$ is halophenyl,
R$^3$ is indolylcarbonyl and
A is (C$_1$–C$_4$)alkylene.

6. A compound of claim 5, which is (6S)-1-methyl-5-oxo-6-(2-indolylcarbonylamino)-8-(2-fluorophenyl)-2,3,5,6-tetrahydro-1H-[1,4]-diazepino[1,7,6-de]quinoxaline.

7. A process for preparing a compound of the formula:

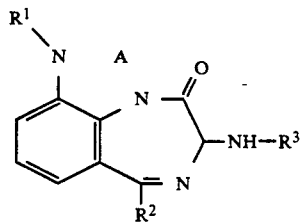

wherein
R$^1$ is hydrogen, or an organic group selected from the group consisting of lower alkyl, lower alkenyl, lower alkynyl, phenyl, naphthyl and phenyl(lower)alkyl,
R$^3$ is phenyl or naphthyl, each of which may have from 1 to 3 substituents selected from the group consisting of halogen, amino, lower alkoxy and mono di or tri halo(lower)alkyl,
R$^3$ is hydrogen, or an acyl group selected from the group consisting of carbamoyl, C1 to C20 alkanoyl, C2 to C20 alkoxycarbonyl, C1 to C20 alkanesulfonyl, C1 to C20 alkoxysulfonyl, benzoyl, naphthoyl, phenyl(lower)alkanoyl, naphthyl(lower)alkanoyl, phenyl(lower)alkenoyl, naphthyl(lower)alkenoyl, phenyl(lower)alkoxycarbonyl, phenoxycarbonyl, naphthyloxycarbonyl, phenylcarbamoyl, naphthylcarbamoyl, phenylthiocarbamoyl, phenylglyoxyloyl, naphthylglyoxyloyl, benzenesulfonyl, heterocyclicglyoxyloyl, heterocyclic(lower)alkanoyl, heterocyclic(lower)alkenoyl and heterocycliccarbonyl wherein said heterocyclic moiety is selected form the group consisting of pyrrolyl, pyrrolinyl, imidazolyl, pyrazolyl, pyridyl, dihydropyridyl, pyrimidyl, pyrazinyl, pyridazinyl, triazolyl, tetrazolyl, pyrrolidinyl, imidazolidinyl, piperidino, piperazinyl, indolyl, isoindolyl, indolinyl, indolizinyl, benzimidazolyl, quinolyl, isoquinolyl, indazolyl, benzotriazolyl, cinnolinyl, quinoxalinyl, oxazolyl, isoxazolyl, oxadiazolyl, morpholinyl, sydnonyl, benzoxazolyl, benzoxadiazolyl, thiazolyl, isothiazolyl, thiadiazolyl, dihydrothiazinyl, thiazolidinyl, thienyl, dihydrodithiinyl, dihydrodithionyl, benzothiazolyl, benzothiadiazolyl, furyl, dihydrooxathiinyl, benzothienyl, benzodithiinyl and benzoxathiinyl, and said acyl group may have from 1 to 10 substituents selected from the group consisting of halogen, hydroxy, nitro, lower alkyl, amino, lower alkoxycarbonylamino, lower alkoxy, carboxy, N,N-di(lower)alkylamino(-lower)alkyl, hydroxyimino(lower)alkyl, phenylimino(lower)alkyl, lower alkanoyl, mono di or tri halo(lower)alkyl and phenylamino, and A is ethylene, or a salt thereof, which comprises (1) reacting a compound of the formula:

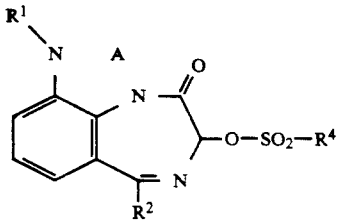

wherein $R^1$, $R^2$ and A are each as defined above, and $R^4$ is an organic group, selected from the group consisting of lower alkyl, lower alkenyl, lower alkynyl, phenyl, naphthyl and phenyl(lower)alkyl or a salt thereof with a compound of the formula:

NH₃ or a salt thereof to give a compound of the formula:

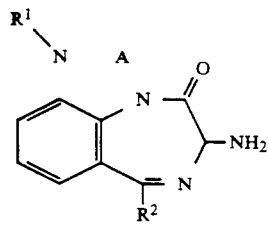

wherein $R^1$, $R^2$ and A are each as defined above, or a salt thereof, or (2) subjecting a compound of the formula:

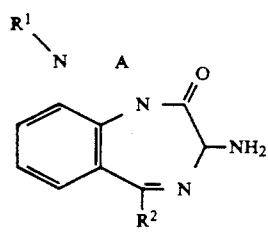

wherein $R^1$, $R^2$ and A are each as defined above, or its reactive derivative at the amino group, or a salt thereof to acylation reaction to give a compound of the formula:

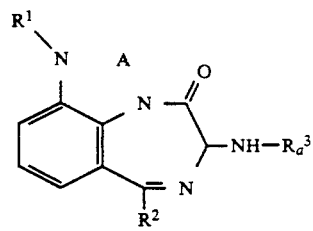

wherein $R^1$, $R^2$ and A are each as defined above, $R_a{}^3$ is an acyl group selected from the group consisting of carbamoyl, C1 to C20 alkanoyl, C2 to C20 alkoxycarbonyl, C1 to C20 alkanesulfonyl, C1 to C20 alkoxysulfonyl, benzoyl, naphthoyl, phenyl(-lower)alkanoyl, naphthyl(lower)alkanoyl, phenyl(-lower)alkenoyl, naphthyl(lower)alkenoyl, phenyl(-lower)alkoxycarbonyl, phenoxycarbonyl, naphthyloxycarbonyl, phenylcarbamoyl, naphthylcarbamoyl, phenylthiocarbamoyl, phenylglyoxyloyl, naphthylglyoxyloyl, benzenesulfonyl, heterocyclic glyoxyloyl, heterocyclic(lower)alkanoyl, heterocyclic(lower)alkenoyl, and heterocyclic carbonyl wherein said heterocyclic moiety is selected form the group consisting of pyrrolyl, pyrrolinyl, imidazolyl, pyrazolyl, pyridyl, dihydropyridyl, pyrimidyl, pyrazinyl, pyridazinyl, triazolyl, tetrazolyl, pyrrolidinyl, imidazolidinyl, piperidino, piperazinyl, indolyl, isoindolyl, indolinyl, indolizinyl, benzimidazolyl, quinolyl, isoquinolyl, indazolyl, benzotriazolyl, cinnolinyl, quinoxalinyl, oxazolyl, isoxazolyl, oxadiazolyl, morpholinyl, sydnonyl, benzoxazolyl, benzoxadiazolyl, thiazolyl, isothiazolyl, thiadiazolyl, dihydrothiazinyl, thiazolidinyl, thienyl, dihydrodithiinyl, dihydrodithionyl, benzothiazolyl, benzothiadiazolyl, furyl, dihydrooxathiinyl, benzothienyl, benzodithiinyl and benzoxathiinyl, and said acyl group may have from 1 to 10 substituents selected from the group consisting of halogen, hydroxy, nitro, lower alkyl, amino, lower alkoxycarbonylamino, lower alkoxy, carboxy, N,N-di(lower)alkylamino(lower)alkyl, hydroxyimino(lower)alkyl, phenylimino(lower)alkyl, lower alkanoyl, mono, di or trihalo(lower)alkyl and phenylamino, or a salt thereof, or (3) subjecting a compound of the formula:

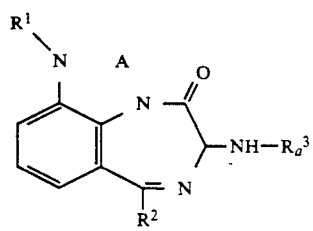

wherein $R^1$, $R^2$, $R_a{}^3$ and A are each as defined above, or a salt thereof to deacylation reaction to give a compound of the formula:

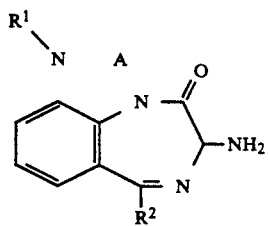

wherein $R^1$, $R^2$ and A are each as defined above, or a salt thereof.

8. A pharmaceutical composition which comprises, as an active ingredient, an effective amount of a compound of claim 1 or a pharmaceutically acceptable salt thereof in admixture with pharmaceutically acceptable carriers.

9. A process of administering a cholecystokinin antagonist to a patient comprising administering an effective amount of a compound of claim 1 or a pharmaceutically acceptable salt to a patient in need thereof.

10. A process of treating or preventing cholecystokinin-mediated diseases which comprises administering an effective amount of a compound of claim 1 or a pharmaceutically acceptable salt thereof to a human or animal.

* * * * *

UNITED STATES PATENT AND TRADEMARK OFFICE
CERTIFICATE OF CORRECTION

PATENT NO. : 5,322,842

DATED : June 21, 1994

INVENTOR(S) : Yoshinari SATO, et al.

It is certified that error appears in the above-indentified patent and that said Letters Patent is hereby corrected as shown below:

Title page, item 57, " 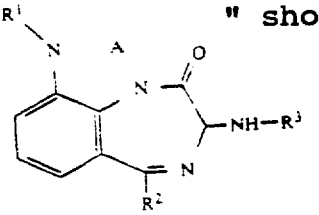 " should read

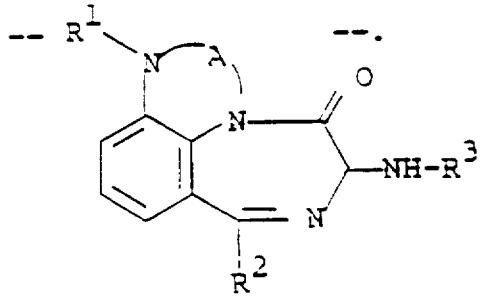

Column 1, lines 36-44, " 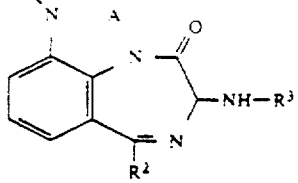 " should read

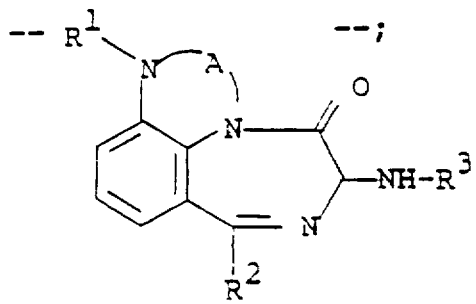

UNITED STATES PATENT AND TRADEMARK OFFICE
CERTIFICATE OF CORRECTION

PATENT NO. : 5,322,842

DATED : June 21, 1994

INVENTOR(S) : Yoshinari SATO, et al.

It is certified that error appears in the above-indentified patent and that said Letters Patent is hereby corrected as shown below:

Column 1, lines 57-65, " 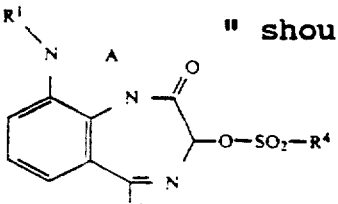 " should read

-- 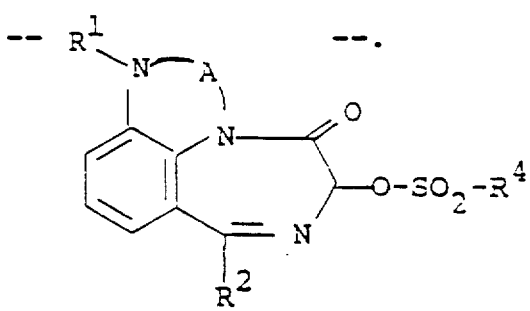 --.

Column 2, lines 3-10, " 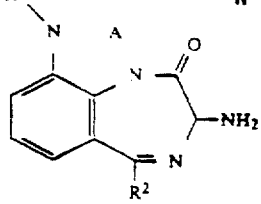 " should read

-- 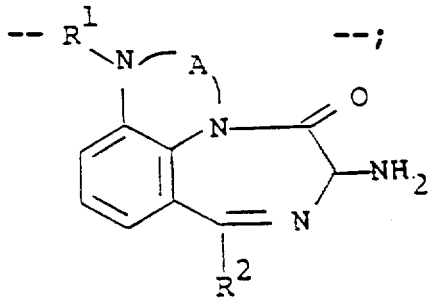 --;

UNITED STATES PATENT AND TRADEMARK OFFICE
CERTIFICATE OF CORRECTION

PATENT NO. : 5,322,842
DATED : June 21, 1994
INVENTOR(S) : Yoshinari SATO, et al.

It is certified that error appears in the above-indentified patent and that said Letters Patent is hereby corrected as shown below:

Column 2, lines 16-24, " 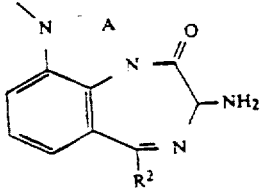 " should read

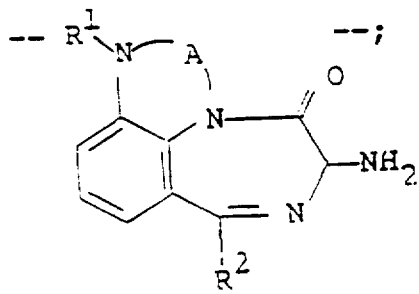 --;

lines 30-37, " 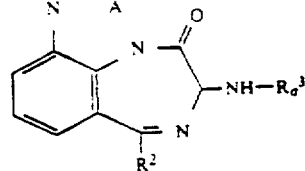 " should read

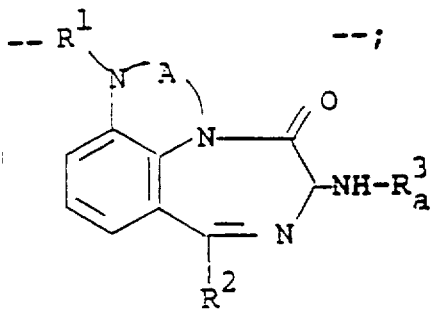 --;

UNITED STATES PATENT AND TRADEMARK OFFICE
CERTIFICATE OF CORRECTION

PATENT NO. : 5,322,842

DATED : June 21, 1994

INVENTOR(S) : Yoshinari SATO, et al.

It is certified that error appears in the above-indentified patent and that said Letters Patent is hereby corrected as shown below:

Column 2, lines 44-51, " 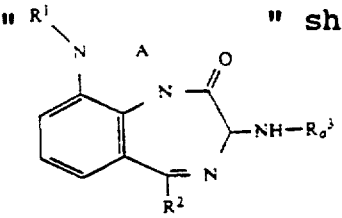 " should read

-- 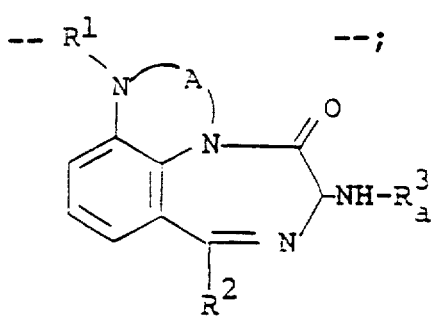 --;

lines 55-63, " 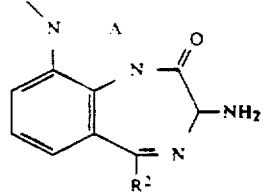 " should read

-- 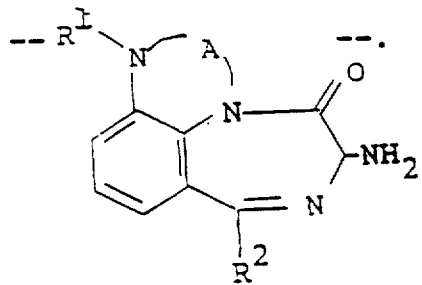 --.

UNITED STATES PATENT AND TRADEMARK OFFICE
CERTIFICATE OF CORRECTION

PATENT NO. : 5,322,842

DATED : June 21, 1994

INVENTOR(S) : Yoshinari, SATO, et al.

It is certified that error appears in the above-indentified patent and that said Letters Patent is hereby corrected as shown below:

Column 3, lines 3-11, " 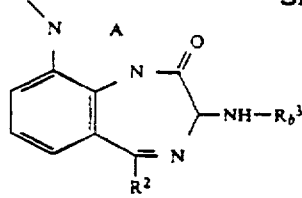 " should read

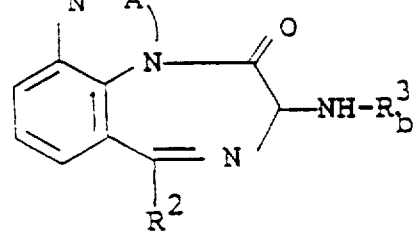 --;

lines 15-23, " 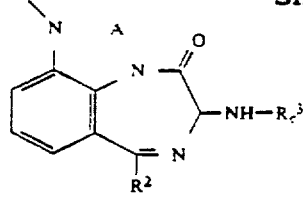 " should read

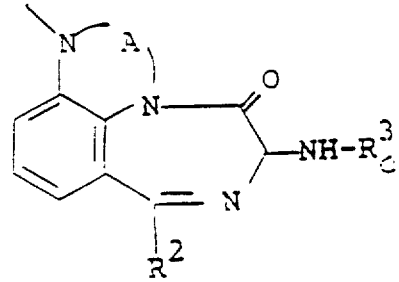 --;

UNITED STATES PATENT AND TRADEMARK OFFICE
CERTIFICATE OF CORRECTION

PATENT NO. : 5,322,842
DATED : June 21, 1994
INVENTOR(S) : Yoshinari SATO, et al.

It is certified that error appears in the above-indentified patent and that said Letters Patent is hereby corrected as shown below:

Column 3, lines 43-49, " 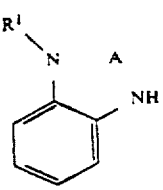 " should read

-- 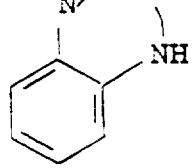 --;

lines 57-63, " 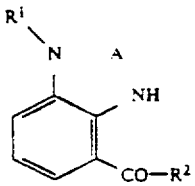 " should read

-- 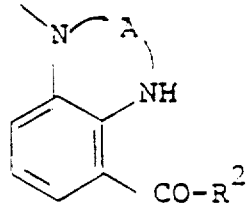 --.

UNITED STATES PATENT AND TRADEMARK OFFICE
CERTIFICATE OF CORRECTION

PATENT NO. : 5,322,842
DATED : June 21, 1994
INVENTOR(S) : Yoshinari SATO, et al.

It is certified that error appears in the above-indentified patent and that said Letters Patent is hereby corrected as shown below:

Column 4, lines 8-14, " 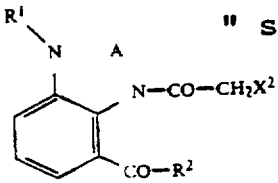 " should read

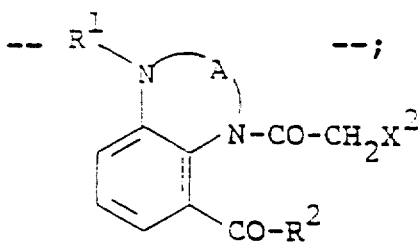 ;

lines 23-32, " 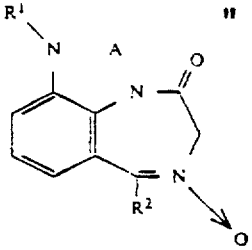 " should read

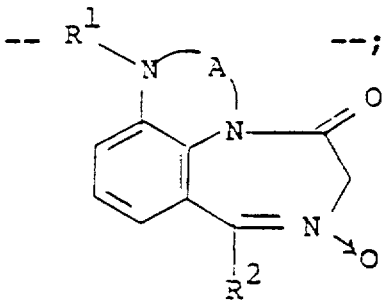 ;

UNITED STATES PATENT AND TRADEMARK OFFICE
CERTIFICATE OF CORRECTION

PATENT NO. : 5,322,842
DATED : June 21, 1994
INVENTOR(S) : Yoshinari SATO, et al.

It is certified that error appears in the above-indentified patent and that said Letters Patent is hereby corrected as shown below:

Column 4, lines 39-47, " 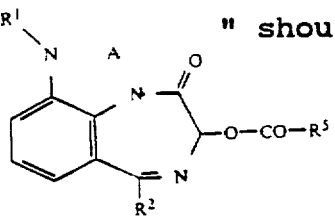 " should read

-- 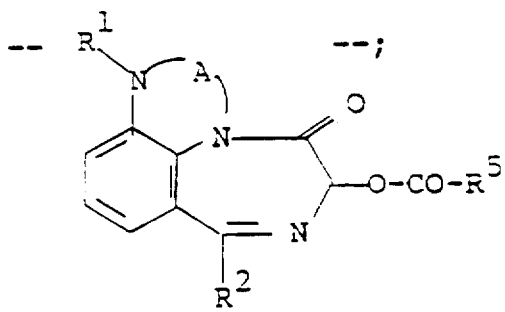 --;

lines 55-63, " 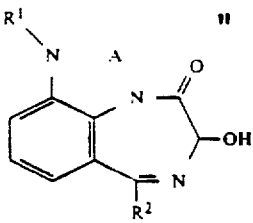 " should read

-- 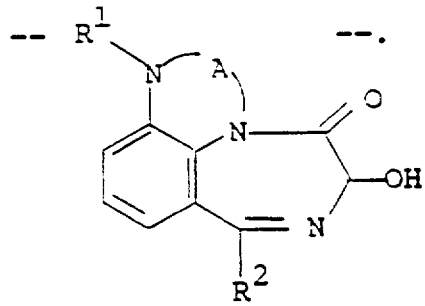 --.

UNITED STATES PATENT AND TRADEMARK OFFICE
CERTIFICATE OF CORRECTION

PATENT NO. : 5,322,842

DATED : June 21, 1994

INVENTOR(S) : Yoshinari SATO, et al.

It is certified that error appears in the above-indentified patent and that said Letters Patent is hereby corrected as shown below:

Column 5, lines 3-11, " 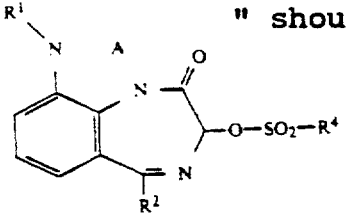 " should read

-- 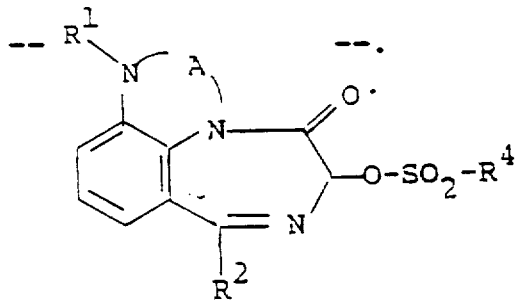 --.

Column 22, lines 39-47, " 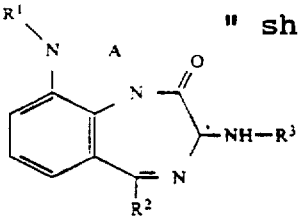 " should read

-- 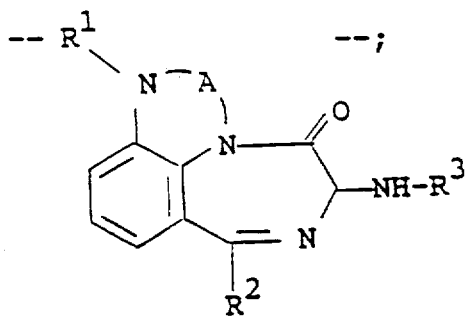 --;

Column 22, line 55, " and mon," should --and mono,--.

UNITED STATES PATENT AND TRADEMARK OFFICE
CERTIFICATE OF CORRECTION

PATENT NO. : 5,322,842
DATED : June 21, 1994
INVENTOR(S) : Yoshinari SATO, et al.

It is certified that error appears in the above-indentified patent and that said Letters Patent is hereby corrected as shown below:

Column 24, lines 25-32, " 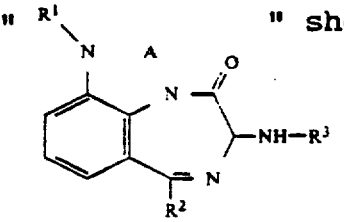 " should read

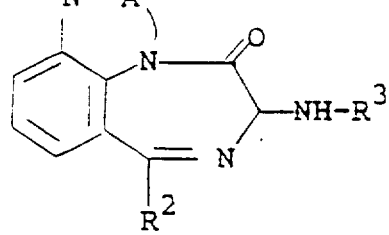 --.

Column 25, lines 16-24, " 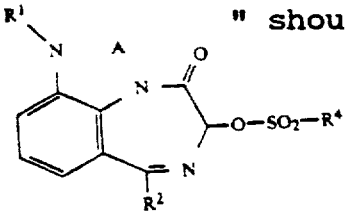 " should read

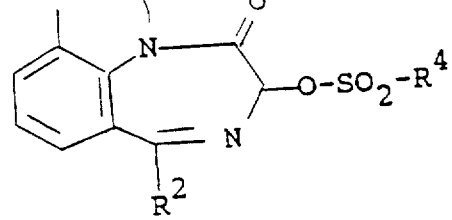 --;

UNITED STATES PATENT AND TRADEMARK OFFICE
CERTIFICATE OF CORRECTION

PATENT NO. : 5,322,842

DATED : June 21, 1994

INVENTOR(S) : Yoshinari SATO, et al.

It is certified that error appears in the above-indentified patent and that said Letters Patent is hereby corrected as shown below:

Column 25, lines 40-47, " 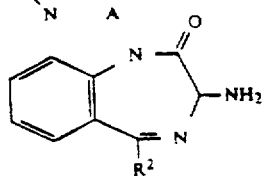 " should read

-- 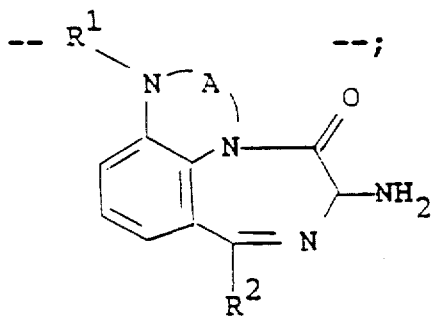 --;

lines 55-63, " 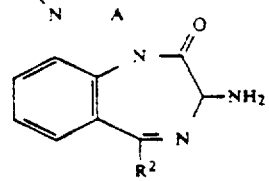 " should read

-- 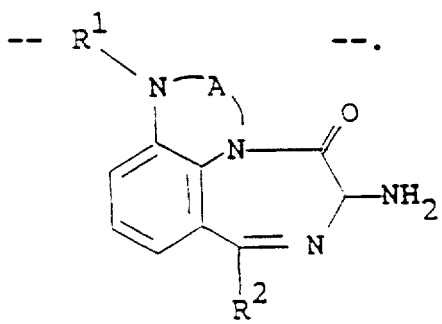 --.

UNITED STATES PATENT AND TRADEMARK OFFICE
CERTIFICATE OF CORRECTION

PATENT NO. : 5,322,842

DATED : June 21, 1994

INVENTOR(S) : Yoshinari SATO, et al.

It is certified that error appears in the above-indentified patent and that said Letters Patent is hereby corrected as shown below:

Column 26, lines 3-11, " 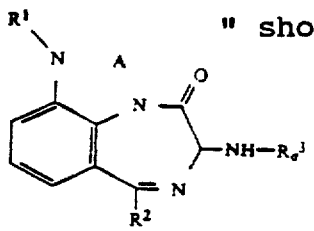 " should read

-- 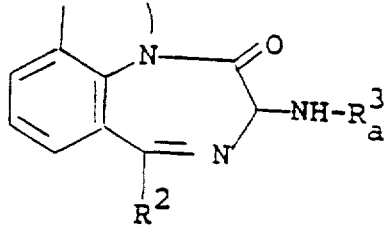 --;

lines 56-64, " 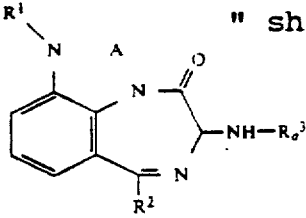 " should read

-- 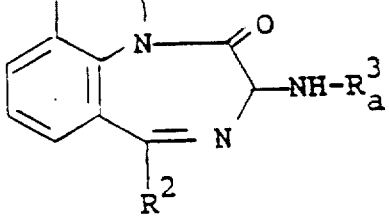 --.

UNITED STATES PATENT AND TRADEMARK OFFICE
CERTIFICATE OF CORRECTION

PATENT NO. : 5,322,842
DATED : June 21, 1994
INVENTOR(S) : Yoshinari SATO, et al.

It is certified that error appears in the above-indentified patent and that said Letters Patent is hereby corrected as shown below:

Column 27, lines 3-10, " " should read

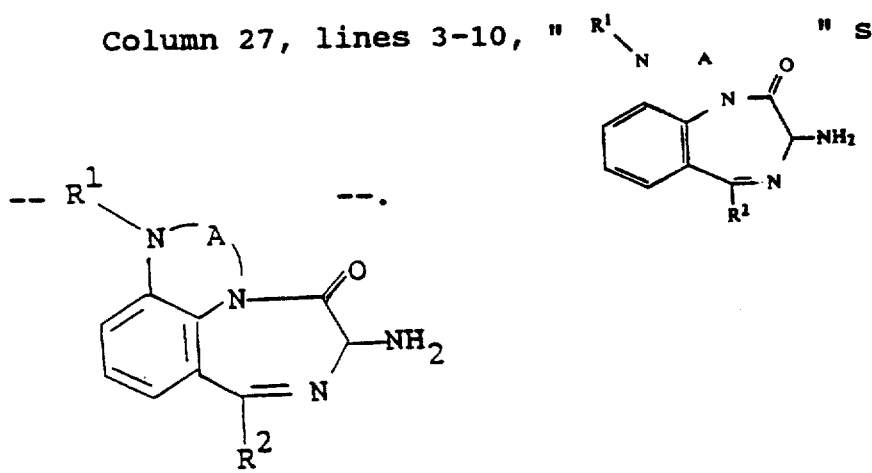

Signed and Sealed this

Fifteenth Day of November, 1994

Attest:

BRUCE LEHMAN

Attesting Officer  Commissioner of Patents and Trademarks